United States Patent
Osypka

(10) Patent No.: US 8,145,315 B2
(45) Date of Patent: Mar. 27, 2012

(54) LEAD ADAPTOR HAVING LOW RESISTANCE CONDUCTORS AND/OR ENCAPSULATED HOUSING

(75) Inventor: Thomas P. Osypka, Palm Harbor, FL (US)

(73) Assignee: Oscor Inc, Palm Harbor, FL (US)

(*) Notice: Subject to any disclaimer, the term of this patent is extended or adjusted under 35 U.S.C. 154(b) by 0 days.

(21) Appl. No.: 12/590,866

(22) Filed: Nov. 16, 2009

(65) Prior Publication Data

US 2010/0137956 A1  Jun. 3, 2010

Related U.S. Application Data

(63) Continuation of application No. 11/179,304, filed on Jul. 12, 2005, now Pat. No. 7,904,161, and a continuation-in-part of application No. 10/174,244, filed on Jun. 18, 2002, now Pat. No. 7,128,600.

(60) Provisional application No. 60/647,736, filed on Jan. 27, 2005, provisional application No. 60/337,437, filed on Oct. 22, 2001, provisional application No. 60/338,227, filed on Dec. 6, 2001, provisional application No. 60/378,423, filed on May 7, 2002.

(51) Int. Cl.
   *A61N 1/00* (2006.01)

(52) U.S. Cl. .......... 607/37; 607/116; 607/117; 607/122

(58) Field of Classification Search .................. 607/37, 607/116–117, 122
See application file for complete search history.

(56) References Cited

U.S. PATENT DOCUMENTS

| | | | |
|---|---|---|---|
| 3,974,834 A | 8/1976 | Kane | |
| 4,452,248 A | 6/1984 | Keller, Jr. | |
| 4,479,500 A | 10/1984 | Smits | |
| 4,545,381 A | 10/1985 | Bournay, Jr. et al. | |
| 4,628,934 A | 12/1986 | Pohndorf et al. | |
| 5,007,177 A | 4/1991 | Rieder et al. | |
| 5,007,864 A | 4/1991 | Stutz, Jr. | |
| 5,314,452 A | 5/1994 | Hirschberg et al. | |
| 5,328,442 A | 7/1994 | Levine | |
| 5,358,519 A | 10/1994 | Grandjean | |
| 5,439,391 A | 8/1995 | McEtchin et al. | |
| 5,470,346 A | 11/1995 | Adams | |
| 5,578,067 A | 11/1996 | Ekwall et al. | |

(Continued)

FOREIGN PATENT DOCUMENTS

EP  0428279 A2  5/1991

(Continued)

*Primary Examiner* — Nicole F Lavert
(74) *Attorney, Agent, or Firm* — Scott D. Wofsy; Edwards Wildman Palmer LLP

(57) ABSTRACT

An implantable lead adaptor is disclosed that includes an encapsulated thermoplastic housing defining a proximal end portion and a distal end portion. The proximal end portion has a first receptacle configured to receive a first type of connector assembly associated with a first implantable cardiac lead, and a second receptacle configured to receive a second type of connector assembly associated with a second implantable cardiac lead. An elongated flexible lead portion extends from the distal end portion of the adaptor housing. A connector assembly is operatively associated with a distal end section of the flexible lead portion of the adaptor for connection to an implantable pulse-generating device, such as, for example, an implantable pacemaker or defibrillator. Low resistance conductor wires electrically connect the connector assembly associated with the distal end section of the lead portion with the first and second receptacles of the adaptor housing.

3 Claims, 7 Drawing Sheets

U.S. PATENT DOCUMENTS

| | | |
|---|---|---|
| 5,662,692 A | 9/1997 | Paspa et al. |
| 5,676,694 A | 10/1997 | Boser et al. |
| 5,679,026 A | 10/1997 | Fain et al. |
| 5,948,014 A | 9/1999 | Valikai |
| 6,006,135 A | 12/1999 | Kast et al. |
| 6,018,683 A | 1/2000 | Verness et al. |
| 6,026,567 A | 2/2000 | Swoyer et al. |
| 6,038,463 A | 3/2000 | Laske et al. |
| 6,038,479 A | 3/2000 | Werner et al. |
| 6,038,481 A | 3/2000 | Werner et al. |
| 6,078,839 A | 6/2000 | Carson |
| 6,119,042 A | 9/2000 | Verness et al. |
| 6,192,278 B1 | 2/2001 | Werner et al. |
| 6,285,910 B1 | 9/2001 | Verness et al. |
| 6,295,476 B1 | 9/2001 | Schaenzer |
| 6,343,233 B1 | 1/2002 | Werner et al. |
| 6,400,992 B1 | 6/2002 | Borgersen et al. |
| 6,434,430 B2 | 8/2002 | Borgersen et al. |
| 6,643,550 B2 | 11/2003 | Westlund et al. |
| 6,671,553 B1 | 12/2003 | Helland et al. |
| 6,772,015 B2 | 8/2004 | Dahl et al. |
| 6,801,809 B2 | 10/2004 | Laske et al. |
| 6,895,277 B2 | 5/2005 | Westlund et al. |
| 6,978,185 B2 | 12/2005 | Osypka |
| 6,983,185 B2 | 1/2006 | Ley et al. |
| 7,130,699 B2 | 10/2006 | Huff et al. |
| 7,155,294 B2 | 12/2006 | Alinder |
| 7,225,034 B2 | 5/2007 | Ries et al. |
| 7,289,846 B2 | 10/2007 | Shoberg et al. |
| 7,343,204 B2 | 3/2008 | Schulman et al. |
| 7,343,206 B2 | 3/2008 | Sage et al. |
| 2002/0143380 A1 | 10/2002 | Dahl et al. |
| 2002/0193860 A1 | 12/2002 | Bischoff et al. |
| 2003/0069625 A1 | 4/2003 | Ley et al. |
| 2003/0077943 A1* | 4/2003 | Osypka .................. 439/623 |
| 2003/0120327 A1 | 6/2003 | Tobritzhofer et al. |
| 2003/0139794 A1 | 7/2003 | Jenney et al. |
| 2003/0199953 A1 | 10/2003 | Stolz et al. |
| 2004/0230278 A1 | 11/2004 | Dahl et al. |
| 2004/0260355 A1 | 12/2004 | Holleman et al. |
| 2004/0260373 A1* | 12/2004 | Ries et al. .................. 607/116 |
| 2006/0106443 A1 | 5/2006 | Michael et al. |
| 2006/0190067 A1 | 8/2006 | Wengreen et al. |
| 2007/0027517 A1 | 2/2007 | Bischoff et al. |
| 2007/0168007 A1 | 7/2007 | Kuzma et al. |
| 2007/0213795 A1 | 9/2007 | Bradley et al. |

FOREIGN PATENT DOCUMENTS

| | | |
|---|---|---|
| EP | 506620 A1 | 9/1992 |
| EP | 0599567 A2 | 6/1994 |
| EP | 0911062 A1 | 4/1999 |
| WO | WO-9930772 A2 | 6/1999 |

* cited by examiner

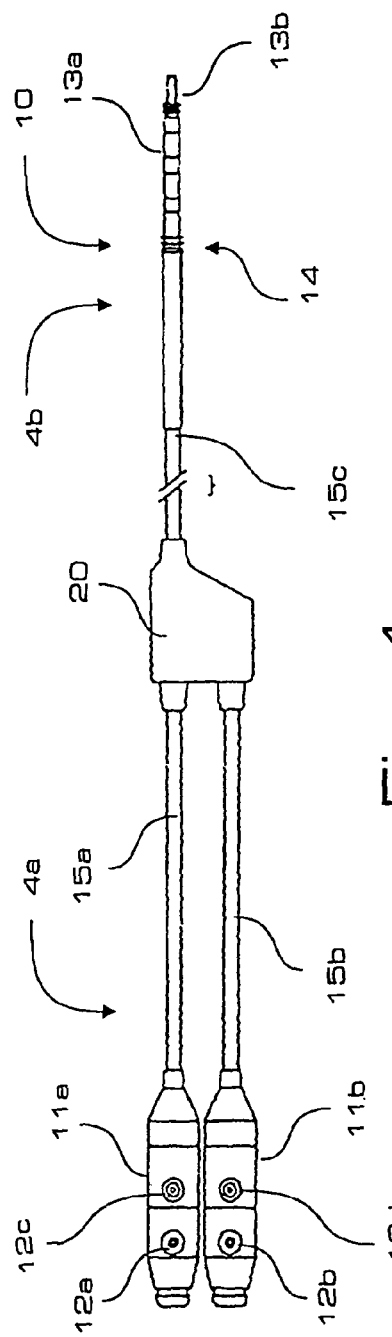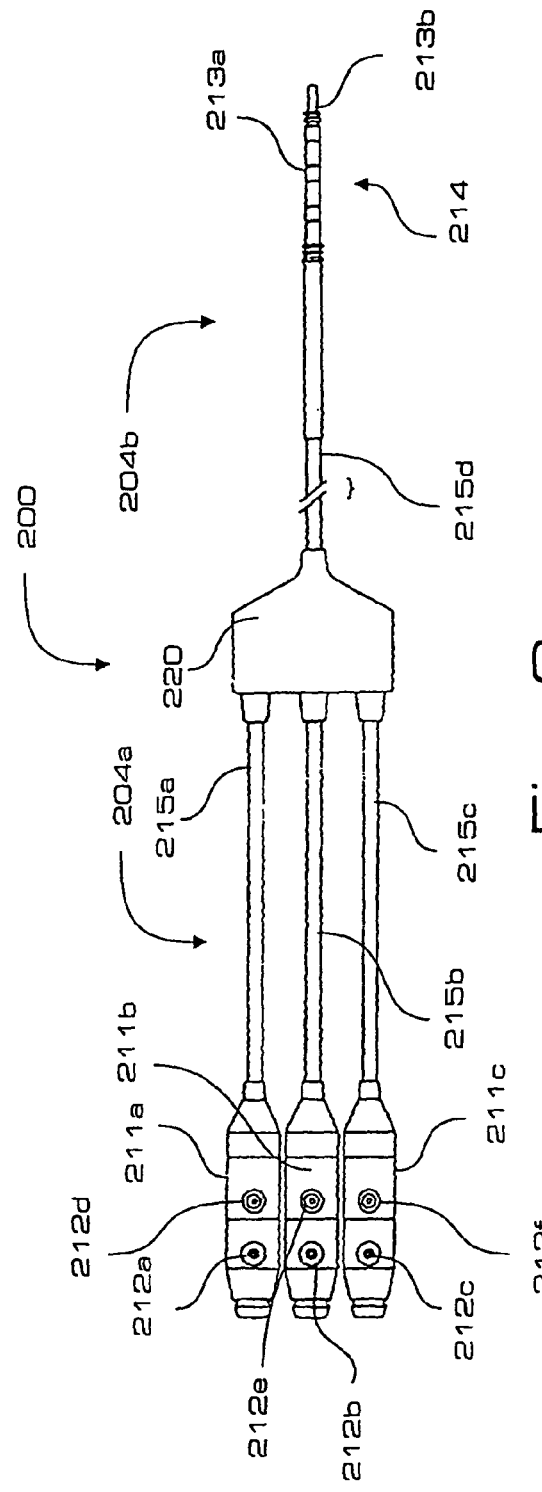

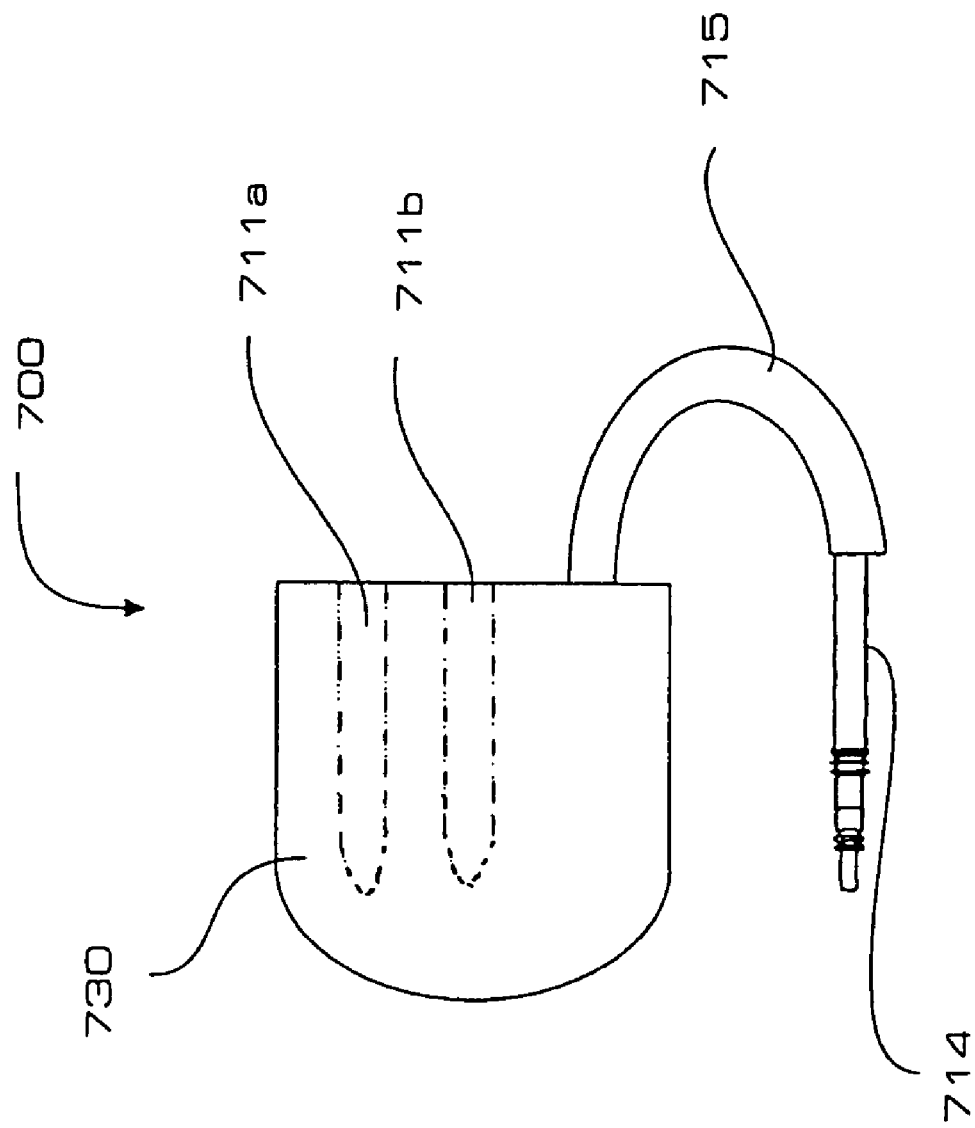

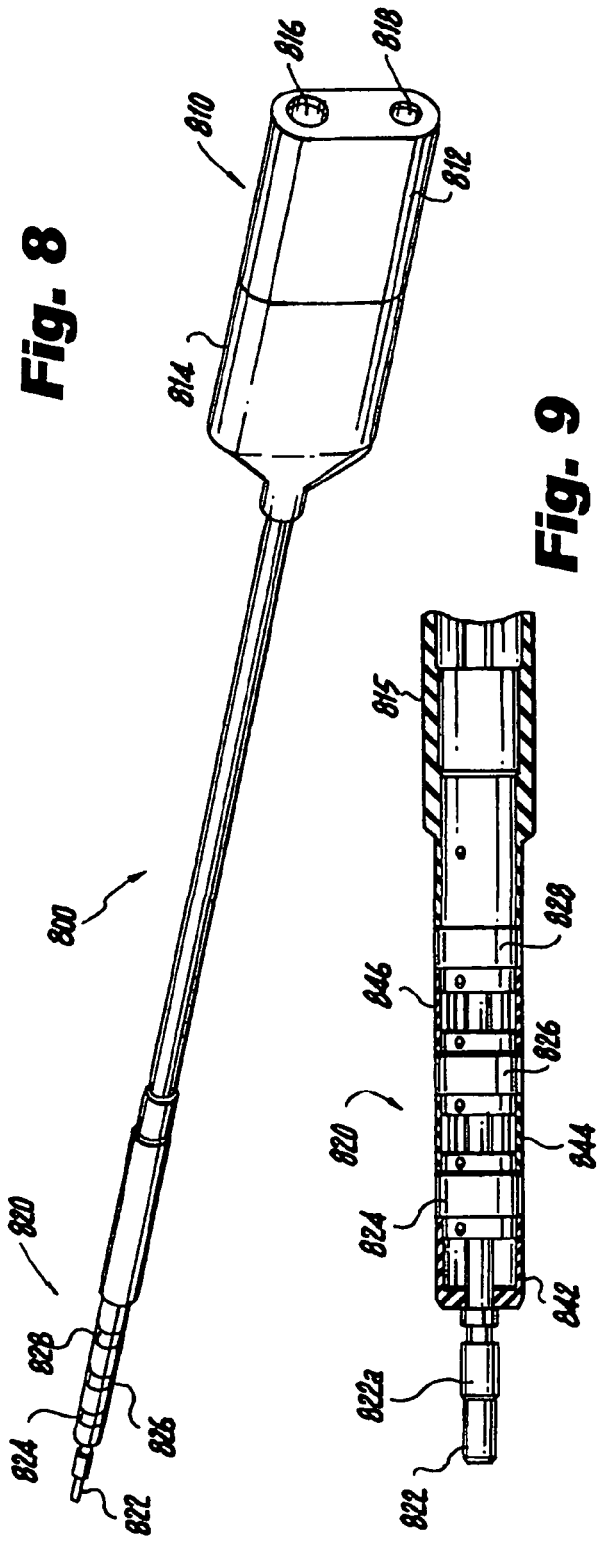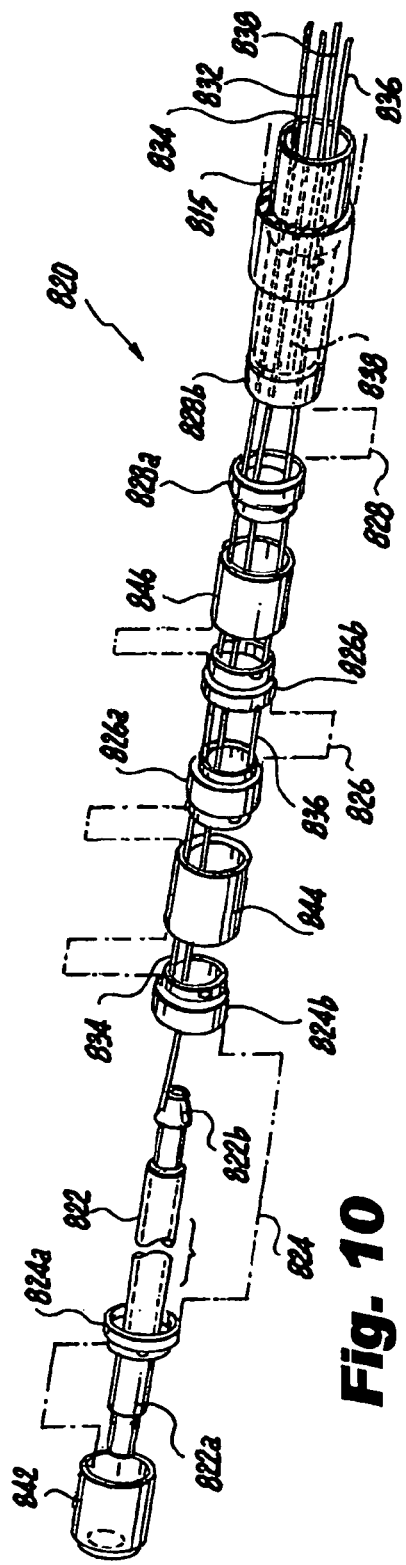

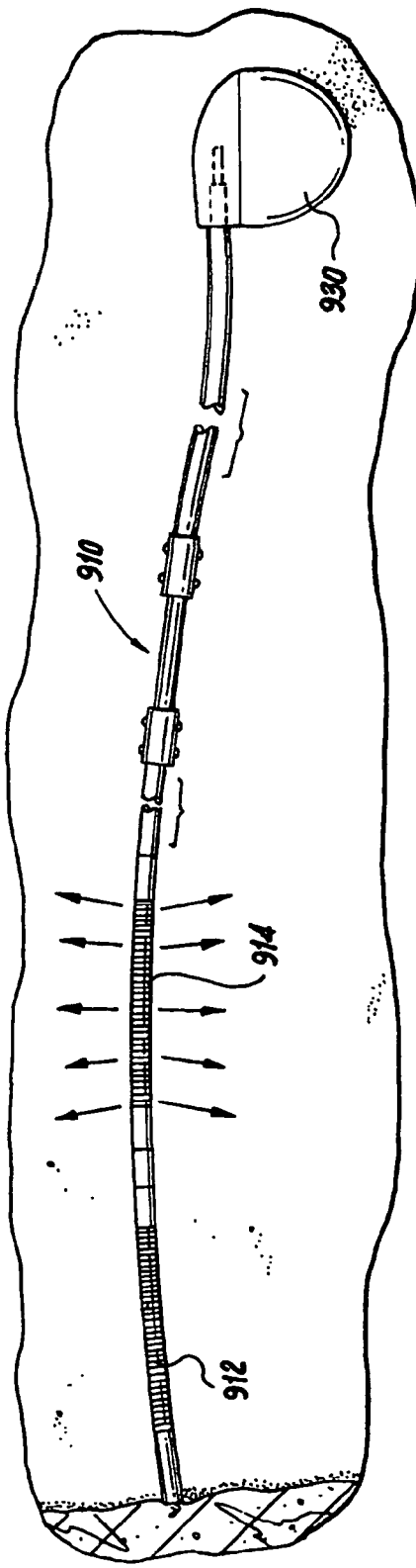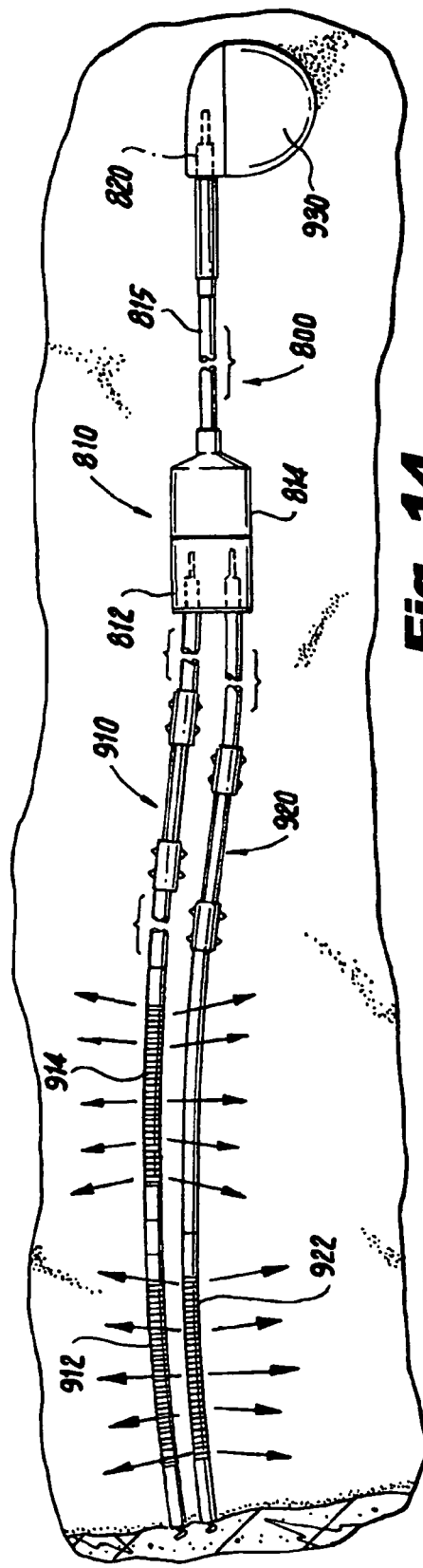

LEAD ADAPTOR HAVING LOW RESISTANCE CONDUCTORS AND/OR ENCAPSULATED HOUSING

CROSS-REFERENCE TO RELATED APPLICATIONS

The subject application is a continuation of U.S. patent application Ser. No. 11/179,304, filed Jul. 12, 2005, now U.S. Pat. No. 7,904,161 which claims the benefit of priority from U.S. Provisional Patent Application 60/647,736, filed Jan. 27, 2005 now abandoned, and is a continuation-in-part of U.S. patent application Ser. No. 10/174,244, filed Jun. 18, 2002, now U.S. Pat. No. 7,128,600, which claims the benefit of priority from U.S. Provisional Patent Application Ser. No. 60/337,437 filed Oct. 22, 2001, now abandoned, U.S. Provisional Patent Application Ser. No. 60/338,227 filed Dec. 6, 2001, now abandoned, and U.S. Provisional Patent Application Ser. No. 60/378,423 filed May 7, 2002, now abandoned, the disclosures of which are all herein incorporated by reference in their entireties.

BACKGROUND OF THE INVENTION

1. Field of the Invention

The subject invention is directed generally to adaptors for electrical stimulation leads, and more particularly, to adaptors for connecting cardiac leads to electrical therapeutic and/or diagnostic devices such as cardiac pacemakers and/or defibrillators.

2. Background of the Related Art

Electrical stimulation devices for cardiac and neurological stimulation are well known in the medical filed. Cardiac stimulation devices are used for therapeutic and/or diagnostic purposes. These devices, which include cardiac pacemakers and implantable cardiac defibrillators, generally interface with cardiac tissue by means of implantable or otherwise attachable cardiac leads. These leads employ connector portions to operatively connect with matching receptacles located in the therapeutic and/or diagnostic devices.

In operation, electrical therapeutic and/or diagnostic devices for the heart send and/or receive electrical signals from heart tissue. These signals are carried to and from the devices through conductors, which form part of the cardiac leads. In order to properly conduct the signals, the cardiac leads must make proper electrical contact with the electrical therapeutic and/or diagnostic devices.

Connectors typically include one or more electrical contact points or poles, to communicate signals between the electrical therapeutic and/or diagnostic device and the leads to which it is connected. These poles are either anodic or cathodic. Anodic poles are generally relatively positive in polarity and cathodic poles are generally relatively negative in polarity.

Connectors are available in various configurations, which are often of standardized types readily recognized by those practicing in the art. Connector types may differ from one another in connector diameter, connector length, connector shape, placement of electrical contact points and other geometric or functional properties. It is well understood by those practicing in the art that connectors of one type cannot directly connect to receptacles designed to operatively accept a different type of connector. Receptacle type is thus determined by the connector type, which the receptacle may operatively accept.

Common connector types well known in the art currently include: IS-I type (International Standard ISO 5841.3:1992) pacing/sensing connectors which have a 3.2 mm diameter and are available in unipolar or bipolar configurations; LV-1 type pacing/sensing connectors which have a 1.8 mm diameter and are available in unipolar and bipolar configurations (Guidant Corporation); and DF-1 type (International Standard ISO 11318:1993) defibrillator connectors which have a unipolar configuration.

Some leads, such as those used in conjunction with implantable cardiac defibrillator (ICD leads), employ multiple connectors. For example, leads are known which employ one or two DF-1 type connectors and one or two IS-1 type connectors, all of which are combined at a yoke portion of the lead.

It is envisioned that other standardized and non-standardized connector types may be developed and utilized in the future as new materials and fabrication techniques are introduced and as specific needs of practitioners change. For example, IS-4 type connectors are being introduced which combine two unipolar DF-1 type connectors and one bipolar IS-1 type connector in a single connector. IS-3 type connectors have also been considered, but have not become standardized.

It is often desirable to utilize more than one lead in conjunction with a single receptacle of an electrical therapeutic and/or diagnostic device. In order to do so, practitioners in the relevant art utilize connection adapters, which generally consist of a connector portion and a receptacle portion. These devices are generally designed to work with only a single connector type; that is, the receptacle portions of these devices are adapted to operatively accept only one type of connector. Utilizing the devices currently known in the art, practitioners are unable to utilize multiple leads having different connector types with a single receptacle of an electrical therapeutic and/or diagnostic device. It would be beneficial therefore, to provide an adapter configured in such a manner so as to enable practitioners to utilize stimulation leads with different types of connectors concurrently with a single receptacle of an electrical therapeutic and/or diagnostic device.

When utilizing two or more cardiac leads with an adaptor, it is often desirable to delay the transmission of electrical signals to one or more of the leads connected to the adapter. For example, adaptors of the present invention are used in some instances for bi-ventricular pacing or re-synchronization of the right and left ventricles in the treatment of congestive heart failure. In these applications, practitioners sometimes desire to introduce a predetermined delay in the delivery of the pacing energy (i.e., the electrical signal) from the electrical therapeutic device to the heart tissue via one or more cardiac leads.

It would therefore be beneficial to provide an adaptor having circuitry for programmatically delaying the transmission of electrical signals from the electrical therapeutic and/or diagnostic device to one or more of the cardiac leads connected to the adaptor, thereby permitting practitioners to control the sequence and timing of the transmission of signals to one or more cardiac leads.

SUMMARY OF THE DISCLOSURE

The subject invention is directed to a new and useful lead adaptor for use in conjunction with electrical stimulation leads such as, for example, cardiac and neurological stimulation leads designed to deliver electrical energy to tissue from an electrical stimulation device. A lead adaptor constructed in accordance with an embodiment of the subject invention includes a connector portion having a connector configured for reception by an electrical stimulation device, and a receptacle portion electrically connected to the connector portion and having at least two receptacles for operatively accepting lead connectors. At least one of the receptacles is configured to operatively accept a different type of lead connector than another receptacle of the receptacle portion.

In one embodiment of the subject invention, the lead adapter includes a centrally located yoke portion, whereby the connector portion extends distally from the yoke portion and the receptacle portion extends proximally from the yoke portion. In another embodiment of the invention, the adaptor includes a housing or block that defines the receptacle portion.

In one embodiment of the subject invention, the receptacle portion of the lead adaptor is bifurcated in that it includes two receptacles. In a first instance, one receptacle is configured to accept a bipolar lead connector and the other receptacle is configured to accept a unipolar lead connector. In another instance, one receptacle is configured to accept a bipolar IS-1 type lead connector and the other receptacle is configured to accept a unipolar IS-1 type lead connector. In yet another instance, one receptacle is configured to accept an IS-1 type lead connector and the other receptacle is configured to accept an LV-1 type lead connector. In still another instance, one receptacle is configured to accept a bipolar IS-1 type lead connector and the other receptacle is configured to accept a unipolar LV-1 type lead connector. In another instance, one receptacle is configured to accept a bipolar IS-1 type lead connector and the other receptacle is configured to accept a bipolar LV-1 type lead connector. In yet another instance, one receptacle is configured to accept a unipolar DF-1 type lead connector and the other receptacle is configured to accept a bipolar IS-1 type lead connector. In certain instances the connector portion of the lead adaptor includes a bipolar IS-1 type lead connector, and in other instances, the connector portion includes a bipolar LV-1 type lead connector. Other types of connectors may also be employed in the lead adaptor.

In another embodiment of the subject invention, the receptacle portion is trifurcated in that it includes three receptacles. In one instance, one receptacle is configured to accept a bipolar lead connector and the other two receptacles are configured to accept unipolar lead connectors. In another instance, one receptacle is configured to accept a unipolar lead connector and the other two receptacles are configured to accept bipolar lead connectors. In yet another instance, one receptacle is configured to accept a bipolar IS-1 type lead connector and the other two receptacles are configured to accept unipolar DF-1 type lead connectors. In still another instance, one receptacle is configured to accept an LV-1 type lead connector and the other receptacles are configured to accept DF-1 type lead connectors. In certain instances the connector portion includes a tripolar in-line connector, and in other instances, the connector portion includes a quadripolar in-line (IS-4 type) connector. Other types of connectors may also be employed in the lead adaptor.

Any of the aforementioned embodiments of the lead adaptor may also contain means for delaying the transmission of electrical signals from the electrical therapeutic and/or diagnostic device to one or more of the endocardial leads attached to the endocardial lead adaptor, thereby allowing predetermined sequencing of electrical signal transmission to the various endocardial leads.

In a preferred embodiment of the subject invention, the lead adaptor includes a yoke portion, a connector portion extending distally from the yoke portion and including a bipolar IS-1 type connector configured for reception within a corresponding port of an electrical stimulation device, and a bifurcated receptacle portion extending proximally from the yoke portion and electrically connected to the connector portion. The receptacle portion includes a first receptacle configured to operatively accept a unipolar LV-1 type lead connector and a second receptacle configured to operatively accept a bipolar IS-1 type lead connector.

In another preferred embodiment of the subject invention, the lead adaptor includes a yoke portion, a connector portion extending distally from the yoke portion and including a bipolar IS-1 type connector configured for reception within a corresponding port of an electrical stimulation device, and a bifurcated receptacle portion extending proximally from the yoke portion and electrically connected to the connector portion. The receptacle portion includes a first receptacle configured to operatively accept a unipolar IS-1 type lead connector and a second receptacle configured to operatively accept a bipolar IS-1 type lead connector.

The subject invention is also directed to an implantable lead adaptor that includes an encapsulated thermoplastic housing defining a proximal end portion and a distal end portion. The proximal end portion of the adaptor housing has a first receptacle configured to receive a first connector assembly associated with a first implantable cardiac lead, and a second receptacle configured to receive a second connector assembly associated with a second implantable cardiac lead. Preferably, the first receptacle is configured to receive a first type of connector assembly and the second receptacle is configured to receive a second type of connector assembly. For example, the first receptacle may be configured to receive a quadripolar DF-4 type connector, whereas the second receptacle may be configured to receive a unipolar DF-1 type connector assembly. Other configuration are also possible and well within the scope of the subject disclosure An elongated flexible lead portion extends from the distal end portion of the adaptor housing. The lead portion is about between 10 cm to 20 cm in length and is preferably formed from silicone or a similar biocompatible material. The lead portion of the adaptor defines a central lumen for accommodating electrical conductors, including, for example, a set of low resistance stranded wires or the like. A connector assembly is operatively associated with a distal end section of the flexible lead portion of the adaptor for connection to an implantable pulse-generating device, such as for example, an implantable pacemaker or defibrillator. Conductor means extending through the lead portion of the adaptor electrically connects the connector assembly associated with the distal end section of the lead portion with the first and second receptacles of the adaptor housing.

Preferably, the adaptor housing is a two-part structure having internal cavities and recesses that define or otherwise form the first and second receptacles, and the housing is encapsulated within an outer hull that is formed from a biocompatible material, such as silicone. The outer hull may a two-part construction or it may be molded over the housing. The conductor means are preferably defined by low resistance wires, and the resistance of each wire is preferably less than 1 ohm. The low resistance wires are preferably either drawn brazed stranded (DBS) wires or drawn filled tube (DFT) wires, and they are preferably formed from a material such as 316L, MP25N, MP35N or alloys thereof. Preferably, the low resistance wires of the conductor means are DFT wires formed by a silver core wire that is clad with MP35N alloy.

In a preferred embodiment of the lead adaptor, the proximal end portion of the adaptor housing has a first receptacle configured to receive a four pole connector assembly (i.e., IS-4 or DF-4) associated with a first implantable cardiac lead and a second receptacle configured to receive a unipolar connector assembly (e.g., IS-1, LV-1 or DF-1) associated with a second implantable cardiac lead. An elongated flexible lead portion extends from the adaptor housing and has a four pole connector assembly (i.e., IS-4 or DF-4) operatively associated with a distal end section thereof. Low resistance conductor wires connect the four pole connector assembly operatively associated with the distal end section of the lead portion with the first and second receptacles of the adaptor housing.

In one exemplary embodiment of the subject invention, the adaptor is configured for use in a situation in which one shocking coil of an implanted double-coiled four pole DF-4 type defibrillation lead has failed, and it is necessary to place a second defibrillation lead having a single coil at the implantation site to assume the role of the failed coil. The second lead in this case is a unipolar DF-1 type defibrillation lead. Accordingly, in this exemplary embodiment of the adaptor, the first receptacle includes four contacts, at least one of which is a high voltage contact associated with the failed defibrillation coil, and the second receptacle includes one high voltage contact for the unipolar lead. The high voltage contact of the first receptacle is connected in parallel to the high voltage contact of the second receptacle. The other three contacts of the first receptacle and the high voltage contact of the second receptacle are connected to the four pole connector assembly operatively associated with the distal end section of the lead portion by the low resistance conductor wires.

These and other aspects of the lead adaptors of the subject invention will become more readily apparent to those having ordinary skill in the art from the following description of the invention taken in conjunction with the drawings described hereinbelow

BRIEF DESCRIPTION OF THE DRAWINGS

So that those having ordinary skill in the art to which the subject invention pertains will more readily understand how to make and use the subject invention, preferred embodiments thereof will be described in detail hereinbelow with reference to the drawings, wherein:

FIG. 1 is a plan view of a bifurcated lead adaptor constructed in accordance with a preferred embodiment of the subject invention;

FIG. 2 is a plan view of a trifurcated lead adaptor constructed in accordance with a preferred embodiment of the subject invention;

FIG. 7 is a plan view of a lead adaptor block constructed in accordance with a preferred embodiment of the subject invention;

FIG. 8 is a perspective view another lead adaptor constructed in accordance with a preferred embodiment of the subject invention, which includes, among other things, an encapsulated housing;

FIG. 9 is a cross-sectional view of the distal end section of the lead portion of the lead adaptor shown in FIG. 8, illustrating the internal components of the four-pole connector assembly associated therewith;

FIG. 10 is an exploded perspective view of the distal end section of the lead portion of the adaptor shown in FIG. 8, with parts separated for ease of illustration;

FIG. 13 is an illustration of an implanted DF-4 type double-coiled defibrillation lead, wherein the distal shocking coil of the lead has malfunctioned; and FIG. 14 is an illustration of an implantable lead adaptor constructed in accordance with a preferred embodiment of the subject invention, employed in conjunction with an implanted defibrillation device, the implanted DF-4 type defibrillation lead shown in FIG. 13, and a unipolar DF-1 type defibrillation lead having a single shocking coil, which replaces and assumes the role of the malfunctioning shocking coil of the previously implanted DF-4 type defibrillation lead.

DETAILED DESCRIPTION OF THE PREFERRED EMBODIMENTS

Figure 3:
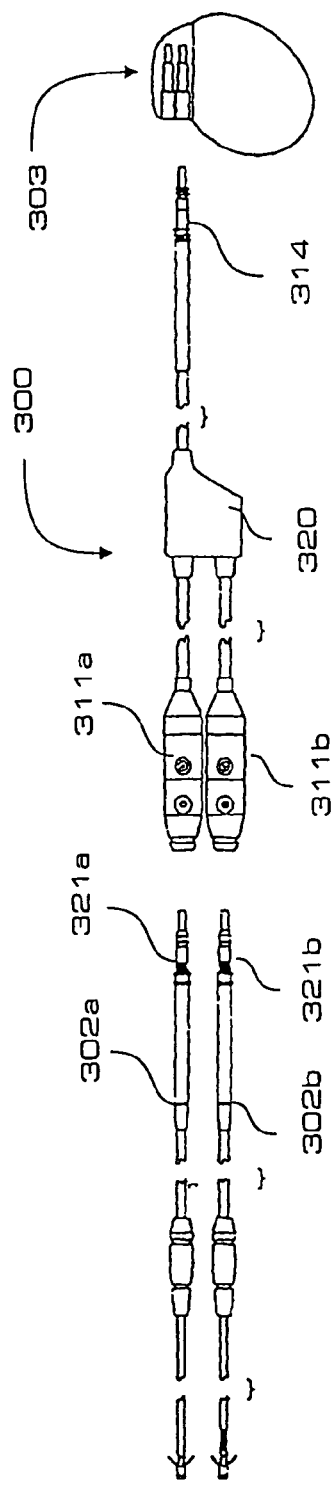
FIG. 3 is a plan view of two leads in position to be operatively connected to a bifurcated lead adaptor of the subject invention, which in turn is in position to be operatively connected to an electrical stimulation device.

Referring now to the drawings wherein like reference numerals identify similar structural features of the several embodiments of the subject invention, there is illustrated in FIG. 1 a lead adaptor constructed in accordance with a preferred embodiment of the subject invention and designated generally by reference numeral 10. Lead adaptor 10 is a bifurcated adaptor and includes a yoke portion 20 from which depends a proximal receptacle portion 4a and a distal connector portion 4b. The receptacle portion 4a includes two receptacles 11a and 11b for operatively receiving two different types of cardiac leads. For example, the leads can have different diameters, different lengths, different shapes or different electrical contact configurations.

In embodiments of the subject invention, the receptacles of the lead adaptors can be configured to operatively accept, among other types of lead connectors, the following types of lead connectors: unipolar or bipolar IS-1 type lead connectors, unipolar or bipolar LV-1 type lead connectors, and unipolar DF-1 type lead connectors. Additionally, the connector portion of the lead adapter of the subject invention can include, among other types of connectors, a bipolar IS-1 type connector, a bipolar LV-1 type connector or a unipolar DF-1 type connector.

With continuing reference to FIG. 1, each receptacle of lead adapter 10 has a number of electrical poles which act as electrical connection points for electrically interfacing with associated cardiac leads. The receptacles are electrically connected to the connector 14 associated with the distal connector portion 4b by way of electrical conductors located in elongated flexible lumens 15a, 15b and 15c communicating with yoke portion 20. While lumens 15a and 15b are shown to have equal lengths, it is envisioned that lumens 15a and 15b can differ in length from one another (see FIG. 6). The electrical conductors contained in each lumen transmit electrical signals between cardiac leads operatively connected with heart tissue and an electrical therapeutic and/or diagnostic device.

Connector 14 of connector portion 4b has a bipolar configuration and includes two poles defined by connector ring 13a and connector pin 13b, respectively. Receptacle poles 12a and 12b and connector ring 13a are cathodic, while receptacle poles 12c and 12d and connector pin 13b are anodic. In particular, receptacle pole 12a of receptacle 1a is electrically connected in parallel with receptacle pole 12b of receptacle 11b, which are then electrically united to cathodic connector ring 13a of connector 14. Similarly, receptacle pole 12c of receptacle 11a is electrically connected in parallel with receptacle pole 12d of receptacle 11b, which are then electrically united with anodic connector pin 13b of connector 14.

In accordance with a preferred embodiment of the subject invention, receptacles 11a and 11b of lead adaptor 10 have different pole dimensions in that receptacle 11a is configured to accept a bipolar lead with a first type of connector, such as a 1.8 mm connector, while receptacle 11b is configured to accept either a unipolar or bipolar lead with a second type of connector, such as an IS-1 (3.2 mm) connector. The connector portion 14 of lead adaptor 10 is defined by a bipolar IS-1 (3.2 mm) connector.

Figure 6:
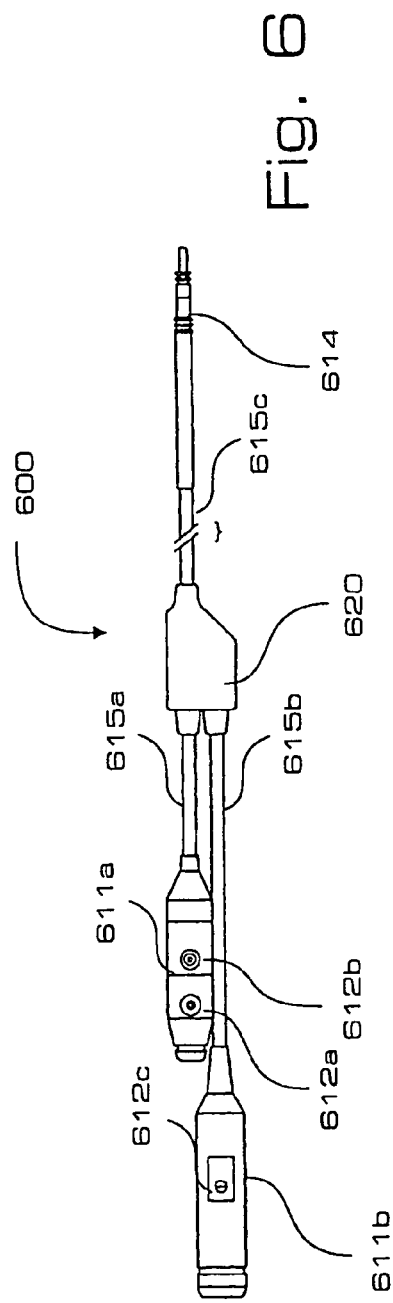
FIG. 6 is a plan view of another lead adaptor constructed in accordance with a preferred embodiment of the subject invention.

It is envisioned that one of the receptacles of lead adaptor 10 can be configured to accept a unipolar lead with an LV-1 (1.8 mm) type connector, as shown for example in FIG. 6. In this instance, the single pole of the unipolar LV-1 receptacle is electrically connected in parallel to the cathodic pole of the bipolar IS-1 (3.2 mm) receptacle, which are then electrically united with the cathodic pole of the connector. The anodic pole of the bipolar IS-1 receptacle is electrically connected to the anodic pole of the connector. It is also envisioned that the connector portion can be defined by a bipolar LV-1 type connector.

Referring now to FIG. 2, there is illustrated another lead adaptor constructed in accordance with a preferred embodiment of the subject invention and designated generally by reference numeral 200. Lead adaptor 200 is known as a trifurcated lead adapter and includes a yoke portion 220 from which extends a proximal receptacle portion 204a and a distal connector portion 204b. The receptacle portion 204a has three receptacles 211a, 211b and 211c each for operatively receiving a cardiac lead to establish electrical connectivity therewith.

Each receptacle is configured for unipolar or bipolar connectivity and includes two poles, 212a-212f, which act as electrical connection points for electrically interfacing with associated leads. The receptacles of receptacle portion 204a are electrically connected to the connector portion 204b by way of electrical conductors located in elongated flexible lumens 215a-215d, which communicate with the yoke portion 220.

The connector portion 204b of lead adaptor 200 includes a bipolar connector 214 having two poles defined by a cathodic connector ring 213a and an anodic connector pin 213b, for establishing and maintaining electrical contact with an electrical therapeutic and/or diagnostic device. Receptacle poles 212a, 212b and 212c are cathodic poles electrically connected in parallel and united at cathodic connector ring 213a of connector 214. Receptacle poles 212d, 212e and 212f are anodic poles electrically connected in parallel and united at the anodic connector pin 213b.

In accordance with a preferred embodiment of the subject invention, two of the three receptacles of lead adaptor 200 may be configured to accept the same type of connector. For example, receptacles 211a and 211b are configured to accept the same type of connector while receptacle 211c is configured to accept a different type of connector. Similarly, receptacles 211a and 211c are configured to accept the same type of connector while receptacle 211b is configured to accept a different type of connector (see FIG. 5). Similarly, receptacles 211b and 211c are configured to accept the same type of connector while receptacle 211a is configured to accept a different type of connector. Alternatively, it is envisioned and well within the scope of the subject disclosure that the receptacles 211a, 211b and 211c are each configured to accept a different type of connector, either one of which might be unipolar or bipolar. In each instance, the connector 214 of connector portion 204b may be defined by a bipolar IS-1 (3.2 mm) type connector or an alternative bipolar connector.

Referring now to FIG. 3, there is illustrated two passive fixation endocardial sensing/pacing leads 302a and 302b in position for operative connection with a bifurcated cardiac lead adaptor constructed in accordance with a preferred embodiment of the subject invention and designated by reference numeral 300. Lead adaptor 300 is in position for operative connection with a cardiac pacemaker 303. In this arrangement, lead 302a is a bipolar lead and has a 3.2 mm IS-1 type connector 321a positioned for operative connection with a bipolar 3.2 mm IS-1 type receptacle 311a of adaptor 300. Upon connection, connector 321a will form an electrical connection with receptacle 311a, thereby permitting electrical signals to travel between receptacle 311a and connector 321a.

In contrast, lead 302b is a unipolar lead and has a larger 6 mm connector 321b positioned for operative connection with the 6 mm receptacle 311b of adaptor 300. Upon connection, connector 321b will form an electrical connection with receptacle 311b, thereby permitting electrical signals to travel between receptacle 311b and connector 321b. As shown, bipolar IS-1 connector 314 extends distally from yoke portion 320 and is positioned to be operatively connected to cardiac pacemaker 303. Upon connection, bipolar IS-1 connector 314 will form an electrical connection with stimulation device 303, thereby permitting electrical signal to travel between device 303 and connector 314.

Figure 4:
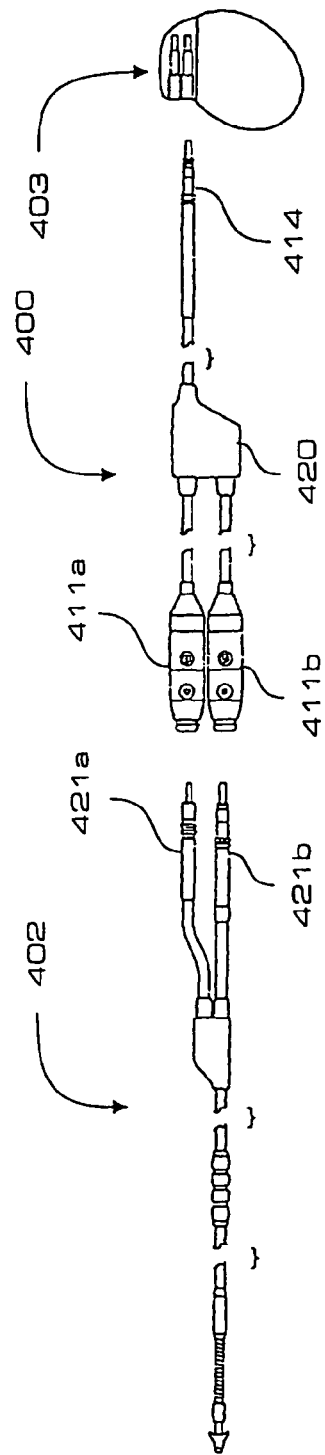
FIG. 4 is a plan view of a bifurcated lead with two connectors in position to be operatively connected to a bifurcated lead adaptor of the subject invention, which in turn is in position to be operatively connected to an electrical stimulation device.

Referring now to FIG. 4, there is illustrated a bifurcated passive fixation endocardial pacing/sensing/defibrillation lead 402 in position for operative connection with a bifurcated lead adaptor constructed in accordance with a preferred embodiment of the subject invention and designated generally by reference numeral 400. Lead adaptor 400 is in position for operative connection with a cardiac pacemaker/implantable cardiac defibrillator 403. The endocardial lead 402 is bifurcated in that is has two connectors 421a and 421b. In this arrangement, connector 421a of lead 402 is a unipolar DF-1 type connector and is in position for operative connection with DF-1 type receptacle 411a of adaptor 400. Upon connection, connector 421a will form an electrical connection with receptacle 411a thereby permitting electrical signal to travel between receptacle 411a, and connector 421a.

In contrast, connector 421b of lead 402 is a bipolar IS-1 type connector and is in position for operative connection with IS-1 type receptacle 411b of adaptor 400. Upon connection, connector 421b will form an electrical connection with receptacle 411b, thereby permitting electrical signal to travel between receptacle 411b and connector 421b. Connector 414 of bifurcated lead adaptor 400, which is preferably defined by a bipolar IS-1 type connector, extends distally from yoke portion 420 and is positioned to be operatively connected to cardiac pacemaker/implantable cardiac defibrillator 403. Upon connection, connector 414 forms an electrical connection with stimulation device 403, thereby permitting electrical signal to travel between device 403 and connector 411.

Figure 5:
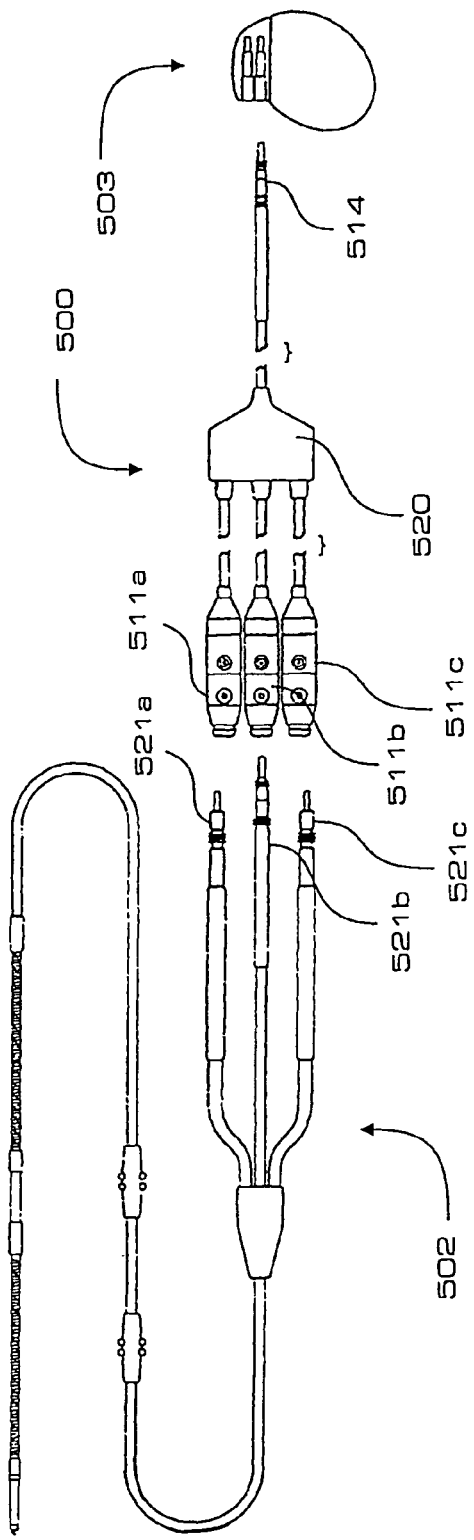
FIG. 5 is a plan view of a trifurcated lead with three connectors in position to be operatively connected to a trifurcated lead adaptor of the subject invention, which in turn is in position to be operatively connected to an electrical stimulation device.

Referring to FIG. 5, there is illustrated an active fixation dual coil endocardial sensing/defibrillation lead 502 in position for operative connection with a trifurcated endocardial lead adaptor constructed in accordance with a preferred embodiment of the subject invention and designated generally by reference numeral 500. Lead adaptor 500 is in position for operative connection with an implantable cardiac defibrillator 503. Endocardial lead 502 is trifurcated in that it has three connectors 521a, 521b and 521c. By way of example, connector 521a is unipolar DF-1 type connector, connector 511b is a bipolar IS-1 type connector, and connector 521c is a second unipolar DF-1 type connector. Accordingly, trifurcated lead adaptor 500 is configured such that receptacle 511a accepts a unipolar DF-1 type connector, receptacle 521b accepts a bipolar IS-1 type connector, and receptacle 511c accepts a unipolar DF-1 type connector. Those skilled in the art will readily appreciate that other combinations of connectors and receptacles can be arranged, and that receptacles 521a, 521b and 521c of adaptor 500 can be configured to accept unipolar or bipolar connectors.

Connector 514 of trifurcated lead adaptor 500, which is preferably defined by an inline multipolar connector (e.g., a quadripolar or IS-4 type connector), extends distally from the yoke portion 520 of adaptor 500 and is in position to be operatively connected to cardiac defibrillator 503. Upon connection, multipolar in-line connector 514 forms an electrical connection with cardiac defibrillator 503, thereby permitting electrical signal to travel between cardiac defibrillator 503 and connector 514.

Referring to FIG. 6, there is illustrated another endocardial lead adaptor constructed in accordance with a preferred embodiment of the subject invention and designated generally by reference numeral 600. Lead adaptor 600 includes a yoke portion 620 from which extends two receptacles 611a and 611b. Receptacles 611a and 611b communicate with yoke portion 620 through corresponding flexible lumens 615a and 615b, respectively. Receptacle 611a is configured to operatively accept a bipolar IS-1 (3.2 mm) type lead connector, while receptacle 611b is configured to operatively accept a unipolar LV-1 (1.8 mm) type lead connector.

Receptacle 611a includes a cathodic pole 612a connected in parallel to the cathodic pole 612c of receptacle 611b and united at the cathodic pole of bipolar IS-1 type connector 614, while the anodic pole 612b of receptacle 611a is connected to the anodic pole of bipolar IS-1 type connector 614. Connector 614 communicates with yoke portion 620 by way of a flexible lumen 615c.

Referring now to FIG. 7, there is illustrated a lead adaptor block constructed in accordance with a preferred embodiment of the subject invention and designated generally by reference numeral 700. Adaptor block 700 includes a main housing 730 that defines a receptacle portion having two receptacles 711a and 711b configured to operatively accept lead connectors, and a connector 714 associated with the distal end of an elongated flexible lumen 715 extending from main housing 730.

Receptacles 711a and 711b of adaptor block 700 are configured to accept two different types of lead connectors. For example, receptacle 711a can be configured to accept a unipolar LV-1 type receptacle, while receptacle 711b can be configured to accept a bipolar IS-1 type lead connector. Alternatively, receptacle 711a can be configured to accept a unipolar IS-1 type receptacle, while receptacle 711b can be configured to accept a bipolar IS-1 type lead connector. In another example, receptacle 711a can be configured to accept a bipolar LV-1 type receptacle, while receptacle 711b can be configured to accept a bipolar IS-1 type lead connector. In either instance, the connector 714 could be configured as a bipolar IS-1 type lead connector.

As noted hereinabove, when utilizing two or more endocardial leads with an adaptor of the type disclosed herein, it is often desirable to delay the transmission of electrical signals to one or more of the leads connected to the adaptor. For example, adaptors of the present invention are used in some instances for bi-ventricular pacing or resynchronization of the right and left ventricles in the treatment of congestive heart failure. In these applications, practitioners often desire to introduce a predetermined delay in the delivery of the pacing energy (i.e., the electrical signal) from the electrical therapeutic device to the heart tissue via one or more endocardial leads. This delay is typically less than 500 milliseconds, and may range from nearly 0 milliseconds to 500 milliseconds.

It is envisioned therefore, that lead adaptors constructed in accordance with the subject invention include control circuitry disposed within the yoke portion for programmatically delaying the transmission of electrical signals from the electrical therapeutic and/or diagnostic device to one or more of the leads connected to the adaptor. In doing so, practitioners can control the sequence and timing of the transmission of signals to one or more of the leads.

In each of the lead adaptors disclosed herein, the lumens may be constructed of any suitable bio-compatible insulator material, such as, for example, silicone, and the electrical conductors extending through each lumen may be constructed of any suitable conductive material and may consist of one or more filaments or filars. For example, a conductor may consist of a multifilar conductor coil having four helically wound conductive filars (i.e., a quadrifilar conductor coil). It is further envisioned that the electrical conductors which connect the receptacles with the connector portion of the adaptor can consist of low resistance wires such as, for example, drawn brazed stranded (DBS) wires or drawn filled tube (DFT) wires, and such wires can be formed from a material selected from the group consisting of 316L, MP25N, MP35N and alloys thereof.

Referring now to FIG. 8, there is illustrated an implantable cardiac lead adaptor constructed in accordance with a preferred embodiment of the subject invention and designated generally by reference numeral 800. Lead adaptor 800 includes an encapsulated thermoplastic housing 810 defining a proximal end portion 812 and a distal end portion 814. The proximal end portion 812 has a first receptacle 816 configured to receive a first connector assembly associated with a first implantable cardiac lead, and a second receptacle 818 configured to receive a second connector assembly associated with a second implantable cardiac lead (see FIG. 14). The receptacles include hardware, such as electrical contacts, for providing an electrical interface with connectors associated with the cardiac leads, as discussed in more detail below.

An elongated flexible lead portion 815 extends from the distal end portion 814 of the adaptor housing 810. The lead portion 815 is about between 10 cm to 20 cm in length and is preferably formed from silicone or a similar biocompatible material. The lead portion 815 of adaptor 800 defines a central lumen for accommodating a plurality of electrical conductors, such as a set of low resistance stranded wires and/or one or more multifilar conductor coils.

A connector assembly or system 820 is operatively associated with a distal end section of the flexible lead portion 815 of adaptor 800 for mechanical and electrical connection to the header cavity of an implantable pulse-generating device, such as, for example, an implantable pacemaker or defibrillator (see e.g. defibrillator 930 in FIG. 14). By way example, connector assembly 820 is a four-pole connector assembly (e.g., DF-4 type). This type of connector has four lead contacts, including a distal connector pin 822, a distal contact ring 824, a medial contact ring 826 and a proximal contact ring 828. The four lead contacts are electrically insulated from one another by transition structures described below.

Referring to FIGS. 9 and 10, the distal connector pin 822 has a distal contact zone 822a and a proximal engagement portion 822b for connection with a low resistance conductive wire 832. The distal contact ring 824 is a two-part coupled structure formed by a distal ring section 824a and a proximal ring section 824b. Similarly, the medial contact ring 26 is a two-part coupled structure formed by a distal ring section 826a and a proximal ring section 826b. The proximal contact ring 28 is also a two-part coupled structure that is defined by a distal ring section 828a and a proximal ring section 828b.

Low resistance conductive wires 834, 836 and 838 are respectively connected to contact rings 824, 826 and 828, as best seen in FIG. 10. The wires preferably have a resistance that is less than 1 ohm, however, this is neither a requirement nor a limitation. The conductive wires 832-838 connect the contacts 822-828 to the receptacles 816 and 818 in the distal end portion 814 of adaptor housing 810. The low resistance wires can be drawn brazed stranded (DBS) wires or drawn filled tube (DFT) wires. These wires can be formed from a material such as 316L, MP25N, MP35N and alloys thereof. In one embodiment of lead adaptor 800, the low resistance wires are DFT wires formed by a silver core wire that is clad with MP35N alloy. DFT wires can also be formed with stainless steel cores in accordance with the subject invention.

A distal insulating tube 842 electrically insulates the contact zone 822a of connector pin 822 from the distal contact ring 824. Similarly, insulating tube 844 insulates distal contact ring 824 from medial contact ring 826, and insulating tube 846 insulates medial contact ring 826 from proximal contact ring 828. Those skilled in the art will readily appreciate that the electrical and insulating components of the connector assembly 820 can be affixed together by conventional joining and assembly methods known in the art.

Those skilled in the art will also appreciate that the configuration of the lead contacts can vary in accordance with the ISO standard for four-pole (quadripolar) connector systems (PAC/CTF-N151R3) developed by the Connector Task Force (CTF) of the AAMI Pacemaker Committee, which is incorporated by reference herein in its entirety. That is, a contact can be either a low voltage contact, a high voltage contact or it can have no electrical connection. For example, the connector assembly 820 can have a distal contact pin 822 defining a low voltage electrode, a distal contact ring 824 defining a low voltage electrode, a medial contact ring 826 defining a high voltage electrode and a proximal contact ring 828 having no electrical connection (i.e., DF4-LLHO). Other alternative configurations include DF4-LLHH, DF4-LLHO, DF4-OOHH. In accordance with the ISO standard, adjacent contacts (e.g., contact rings 824, 826) can be electrically common.

Those skilled in the art will further appreciate that the quadripolar connector assembly 820, while described herein by way of a non-limiting example as a DF-4 type connector, could be an IS-4 type quadripolar connector, designed for pacing and sensing, rather than defibrillation. In such instances, the connector assembly 820 could have contact configurations such as IS4-LLLO or IS4-LLLL.

Figure 11:
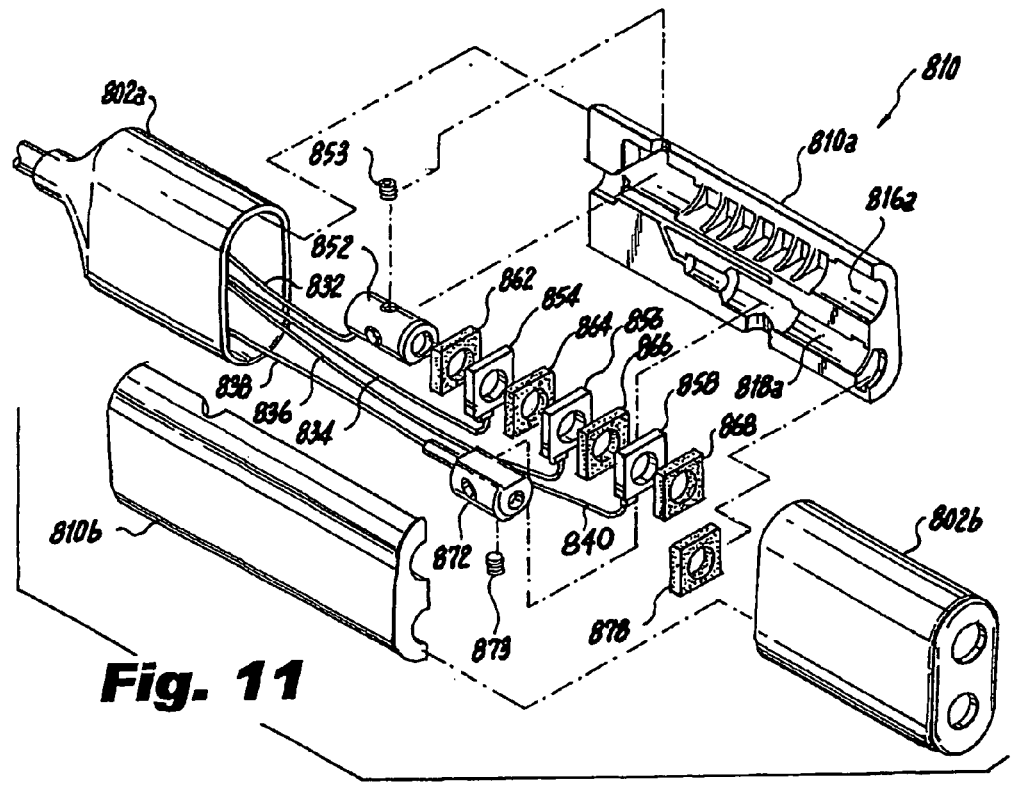
FIG. 11 is an exploded perspective view of the adaptor housing of the lead adaptor shown in FIG. 8, with parts separated for ease of illustration.
Figure 12:
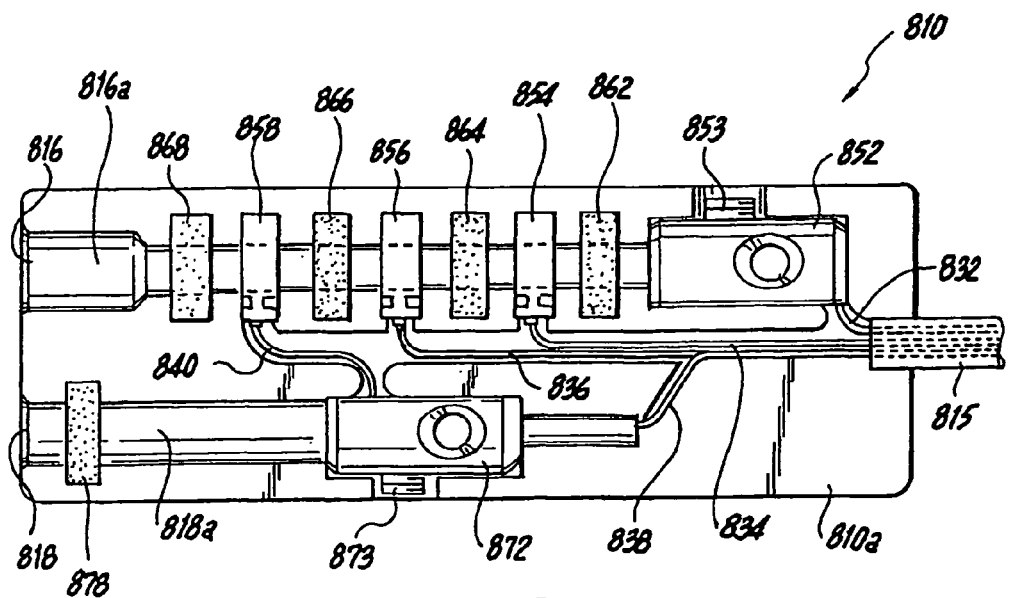
FIG. 12 is a cross-sectional view of the adaptor housing of the lead adaptor shown in FIG. 8, illustrating the assembled location of the each of the component parts thereof.

Referring now to FIGS. 11 and 12, adaptor housing 810 is a two-part structure (810a, 810b) having internal cavities that define or otherwise form the first and second receptacles 816 and 818 and accommodate the mechanical components and conductive wires associated therewith. The two halves 810a, 810b of housing 810 fit together and add stability to the proximal receptacle portion 812 of adaptor housing 810. It also provides a means of easy assembly. Adaptor housing 810 is preferably constructed from a relatively stiff thermoplastic material, such as, for example, polyurethane, tecothane, polycarbonate and/or composites thereof.

Adaptor housing 810 is encapsulated or otherwise enclosed within a two-part outer hull section including a distal hull section 802a and a proximal hull section 802b. The hull sections 802a, 802b are formed from a biocompatible material, such as, for example, silicone or a similar material. The outer hull provides stability for the proximal receptacle portion 812 of the adaptor 800, while offering protection and seal for biocompatibility and long-term reliability. It is envisioned and well within the scope of the subject disclosure that instead of having two separate hull sections enclosing the adaptor housing 810, the housing 810 could be over-molded with the silicone outer hull after it has been assembled using molding techniques known in the art.

The first receptacle 816 of adaptor housing 810 is configured for mechanical and electrical connection with a quadrifilar connector of a cardiac lead, and in this exemplary case, a DF-4 type connector (see FIG. 14). Receptacle 816 includes a series of recesses or cavities that contain a plurality of electrical connectors for accommodating the contacts of a four-pole lead connector. These connectors include a distal pin connector 852 having an associated locking screw 853 which together receive and mechanically secure a distal connector pin of a quadripolar connector; a distal ring connector 854 for receiving and electrically connecting with a distal contact ring of a quadripolar connector; a medial ring connector 856 for receiving and electrically connecting with a medial contact ring of a quadripolar connector; and a proximal ring connector 858 for receiving and electrically connecting with a proximal contact ring of a quadripolar connector.

Ring connectors 854, 856 and 858 are preferably formed at least in part from a material such as titanium, 316L stainless steel, MP35N or the like. More preferably, the connectors 854, 856 and 858 are formed in accordance with the disclosure of co-pending U.S. Provisional Patent Application 60/647,736, which is herein incorporated by reference in its entirety. Accordingly, the connectors 854, 856 and 858 have uniquely designed conductive portions formed from a material such as titanium, 316L stainless steel or MP35N, which are over-molded with a resilient non-conductive material such as silicone that functions to provide a secure mechanical and electrical connection between the connectors and the contacts.

Insulating seals are disposed within a series of recesses defined in the receptacle 816 between adjacent ring contacts. These include a distal insulating seal 862 disposed between pin connector 852 and ring connector 854; a first medial insulating seal 864 disposed between ring connectors 854 and 856; a second medial insulating seal 866 disposed between ring connectors 856 and 858; and a proximal insulating seal 868 disposed proximal to ring connector 858 adjacent the reception bore 816a of receptacle 816.

The second receptacle 818 of adaptor housing 810 is configured for mechanical and electrical connection with a unipolar connector of a cardiac lead, and in this exemplary case, a DF-1 type connector (see FIG. 14). Therefore, receptacle 818 contains one electrical pin connector 872 for receiving the engagement zone of a distal contact pin of a unipolar DF-1 lead connector. Pin connector 872 has an associated locking screw 873 for securing the DF-1 lead connector in place. A seal 878 is located adjacent in the reception bore 818*a* of receptacle 818.

As described above, low resistance conductive wires 832-838 connect the contacts 822-828 of connector assembly 820 to the receptacles 816 and 818 in the distal end portion 814 of adaptor housing 810. In accordance with the exemplary embodiment of the lead adaptor 800 of the subject invention, and for reasons that will be discussed below in conjunction with FIGS. 13 and 14, conductive wire 832 electrically connects the distal pin connector 852 of receptacle 816 with the proximal engagement portion 822*b* of the distal connector pin 822 of connector assembly 820; conductive wire 834 electrically connects the distal connector 854 of receptacle 816 with the distal contact ring 824 of connector assembly 820; conductive wire 836 electrically connects the medial connector 856 of receptacle 816 with the medial contact ring 826 of connector assembly 820. Conductive wire 838 electrically connects the pin connector 872 of receptacle 818 with the proximal contact ring 826 of connector assembly 820. Finally, in this exemplary embodiment of the lead adaptor 800, a fifth low resistance conductive wire 840 parallel connects the pin connector 872 of receptacle 818 with the proximal contact 858 of the receptacle 816.

Referring now to FIGS. 13 and 14, in the exemplary embodiment of the subject invention, lead adaptor 800 is configured for use in a situation in which the distal shocking coil 912 of an implanted DF-4 type defibrillation lead 910 has failed, and it is necessary to implant a second defibrillation lead 920 having a single shocking coil 922 at the same or an adjacent site to assume the role of the failed coil 912, in conjunction with an implanted defibrillator 930. In this instance, the second lead 920 is a unipolar DF-1 type defibrillation lead.

In this exemplary embodiment of the subject invention, the failure mode of the shocking coil 912 relates to the proximal contact ring of the DF-4 type connector associated therewith. This particular failure mode gives rise to the wiring configuration described above and illustrated in FIGS. 11 and 12, wherein the proximal contact 858 of receptacle 816 is connected to the pin connector 872 of receptacle 818 by low resistance wire 840. Under these wiring conditions, the single shocking coil 922 of the DF-1 type defibrillation lead 920 operates in conjunction with the working proximal coil 914 of DF-4 type defibrillation lead 910, to replace the failed shocking coil 912.

Those skilled in the art will readily appreciate that the lead adaptor 800 of the subject invention advantageously enables the continued use of the previously implanted DF-4 defibrillation lead, even after it has malfunctioned in part, as well as the implanted defibrillator, which has a single DF-4 type connector cavity. This reduces trauma to the muscular tissue of the heart and lowers the overall cost of cardiac maintenance.

Those skilled in the art will also appreciate that alternative wiring arrangements with respect to the contacts within the receptacles of the adaptor housing 810 can be easily configured due to the modularity of the connective components, to accommodate a variety of different failure modes associated with a four-pole cardiac lead (i.e., DF-4 or IS-4), aside from the one described hereinabove, by way of non-limiting example.

Those skilled in the art will further appreciate that the modularity of the novel mechanical and electrical connective components contained with the encapsulated adaptor housing 810, as well as the construction of encapsulated two-part (810*a*, 810*b*) adaptor housing itself, are such that the lead adaptor 800 of the subject invention may be used in conjunction with other types of cardiac leads, including, without limitation, cardiac leads having the following types of lead connectors: unipolar or bipolar IS-1 type lead connectors; and unipolar or bipolar LV-1 type lead connectors.

Although the lead adaptors of the subject invention have been described with respect to various embodiments, those skilled in the art will readily appreciate that changes and modifications may be made thereto without departing from the spirit and scope of the present invention as defined by the appended claims.

What is claimed is:

1. A lead adaptor comprising:
   a) a connector portion including a quadrupolar connector assembly configured for reception by an electrical stimulation device; and
   b) a receptacle portion electrically connected to the connector portion and having two receptacles for operatively accepting lead connectors, wherein one of the receptacles of the receptacle portion is configured to operatively accept a lead connector of a first type and the other receptacle of the receptacle portion is configured to accept a lead connector other than the first type.

2. A lead adaptor comprising:
   a) a connector portion including an IS-4 connector assembly configured for reception by an electrical stimulation device;
   b) a receptacle portion electrically connected to the connector portion and having two receptacles for operatively accepting lead connectors, wherein one of the receptacles of the receptacle portion is configured to operatively accept an IS-4 lead connector and the other receptacle of the receptacle portion is configured to accept an IS-1 lead connector.

3. A lead adaptor comprising:
   a) a connector portion including a quadrupolar IS-4 connector assembly configured for reception by an electrical stimulation device;
   b) a receptacle portion electrically connected to the connector portion and having two receptacles for operatively accepting lead connectors, wherein one of the receptacles of the receptacle portion is configured to operatively accept an IS-4 lead connector and the other receptacle of the receptacle portion is configured to accept DF-1 lead connector.

* * * * *